United States Patent [19]

Justin et al.

[11] Patent Number: 5,730,744
[45] Date of Patent: *Mar. 24, 1998

[54] SOFT TISSUE SCREW, DELIVERY DEVICE, AND METHOD

[76] Inventors: Daniel F. Justin, 4544 Trescott Dr., Orlando, Fla. 32817; Thomas F. Winters, Jr., 1800 Summerland Ave., Winter Park, Fla. 32789

[*] Notice: The term of this patent shall not extend beyond the expiration date of Pat. No. 5,503,634.

[21] Appl. No.: 461,870

[22] Filed: Jun. 5, 1995

Related U.S. Application Data

[63] Continuation-in-part of Ser. No. 312,999, Sep. 27, 1994, Pat. No. 5,569,252.
[51] Int. Cl.$^6$ ............................................. A61B 17/68
[52] U.S. Cl. .............................................. 606/73; 606/104
[58] Field of Search ................... 606/73, 104, 72, 606/60, 77, 76, 86, 99, 213, 218, 216, 96, 98; 411/395, 415

[56] References Cited

U.S. PATENT DOCUMENTS

| | | | |
|---|---|---|---|
| Re. 34,871 | 3/1995 | McGuire et al. | 606/73 |
| 4,175,555 | 11/1979 | Herbert . | |
| 4,873,976 | 10/1989 | Schreiber . | |
| 4,884,572 | 12/1989 | Bays et al. . | |
| 4,895,148 | 1/1990 | Bays et al. . | |
| 5,059,206 | 10/1991 | Winters . | |
| 5,152,790 | 10/1992 | Rosenberg | 623/13 |
| 5,169,400 | 12/1992 | Mühling et al. . | |
| 5,259,398 | 11/1993 | Vrespa | 128/898 |
| 5,492,442 | 2/1996 | Lasner . | |

FOREIGN PATENT DOCUMENTS 9416636  8/1994  WIPO .

*Primary Examiner*—Guy V. Tucker
*Attorney, Agent, or Firm*—Allen, Dyer, Doppelt, Milbrath & Gilchrist, P.A.

[57] ABSTRACT

A fastener, driving device, and method are provided for repairing a tear in soft tissue of a patient, such as a meniscal tear in a knee. The fastener has a variable-pitch helical protrusion along a central portion that decreases from the distal end to the proximal end, for bringing two sides of the tear into apposition as the fastener is advanced across the two sides of the tear in a screwing motion. A buttress form of helical protrusion is used for resisting axial forces from pulling the fastener out of the tear and from pulling the two sides of the tear apart. The fastener material preferably is a biodegradable, biocompatible, nontoxic plastic that is specifically designed to biodegrade generally within the time span of the healing process. A delivery device for introducing the fastener is also provided that includes an elongated needle rotationally coupled with the fastener, the turning of which turns the fastener, advancing the fastener into the tissue. The method of repairing the tear entails manipulating the fastener/delivery device system adjacent and normal to the tear axis and driving the fastener across the tear.

13 Claims, 9 Drawing Sheets

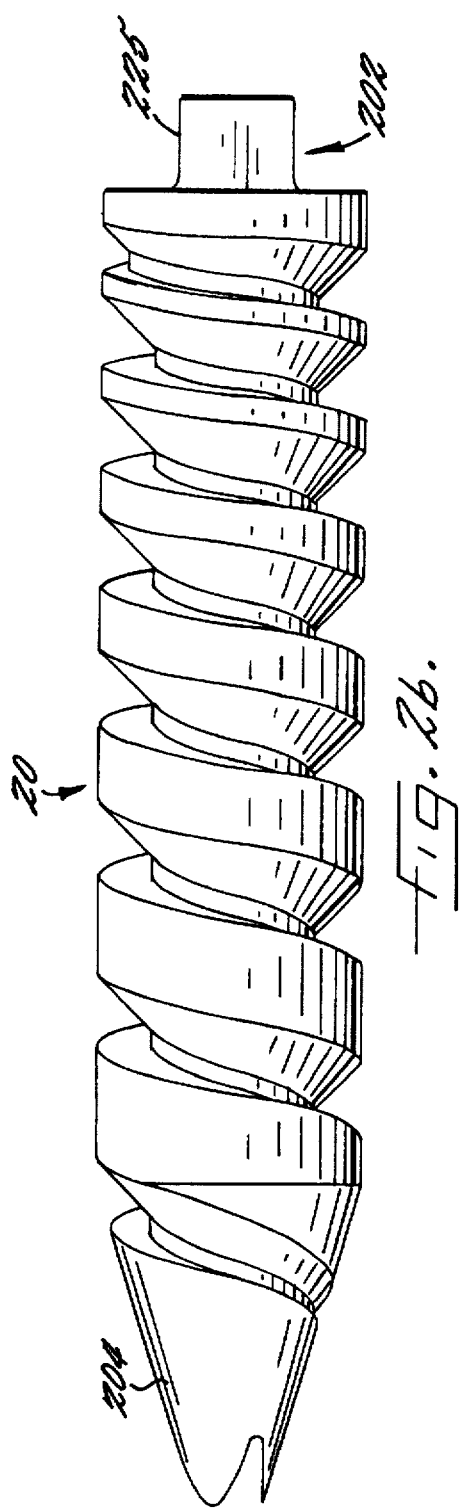
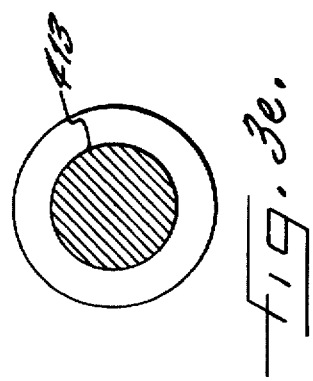
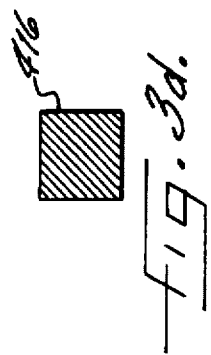
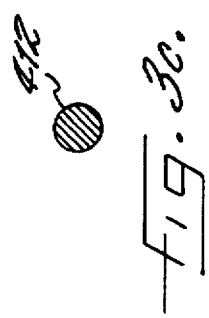
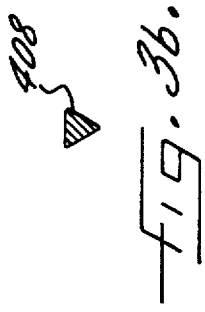

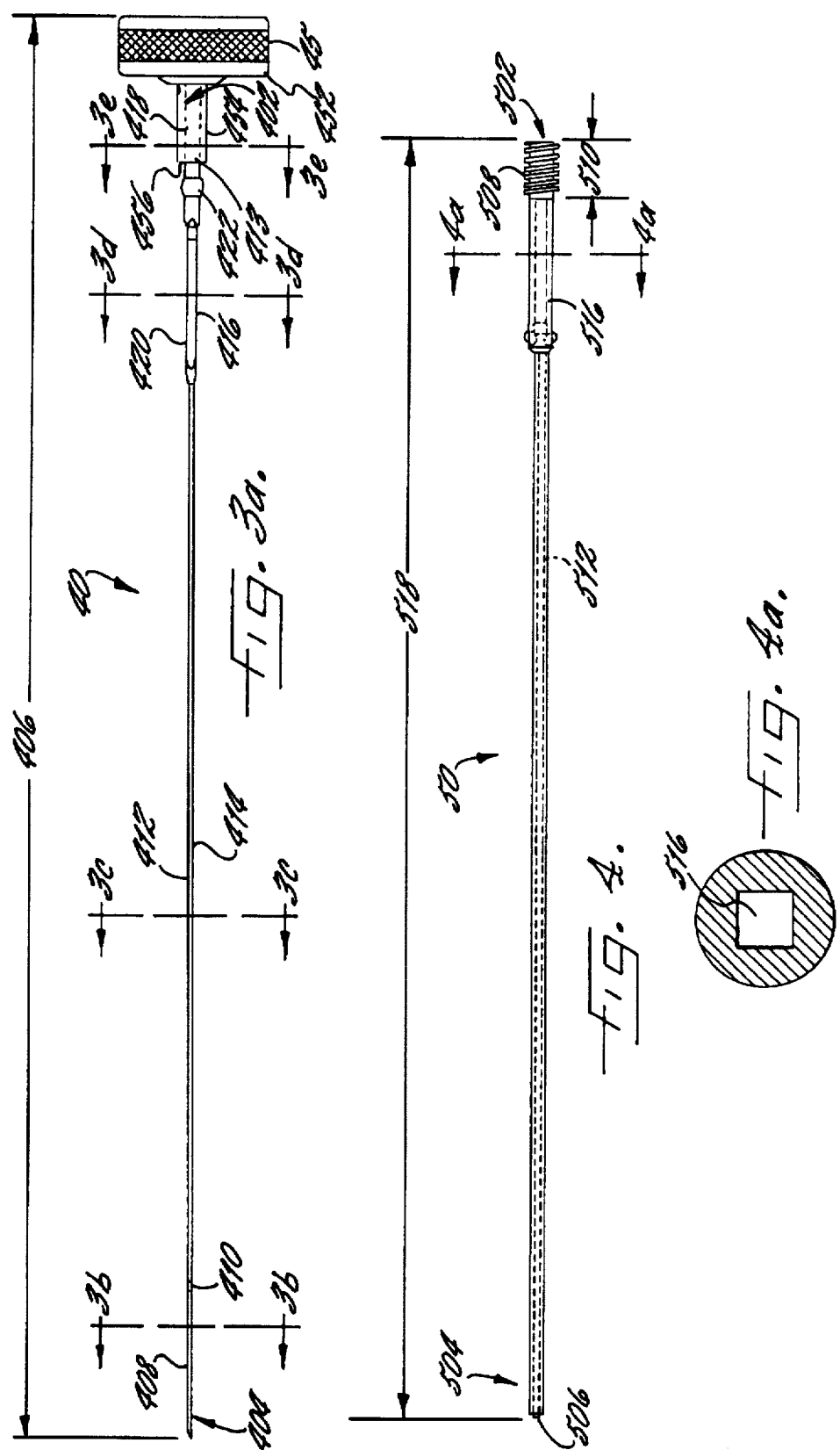

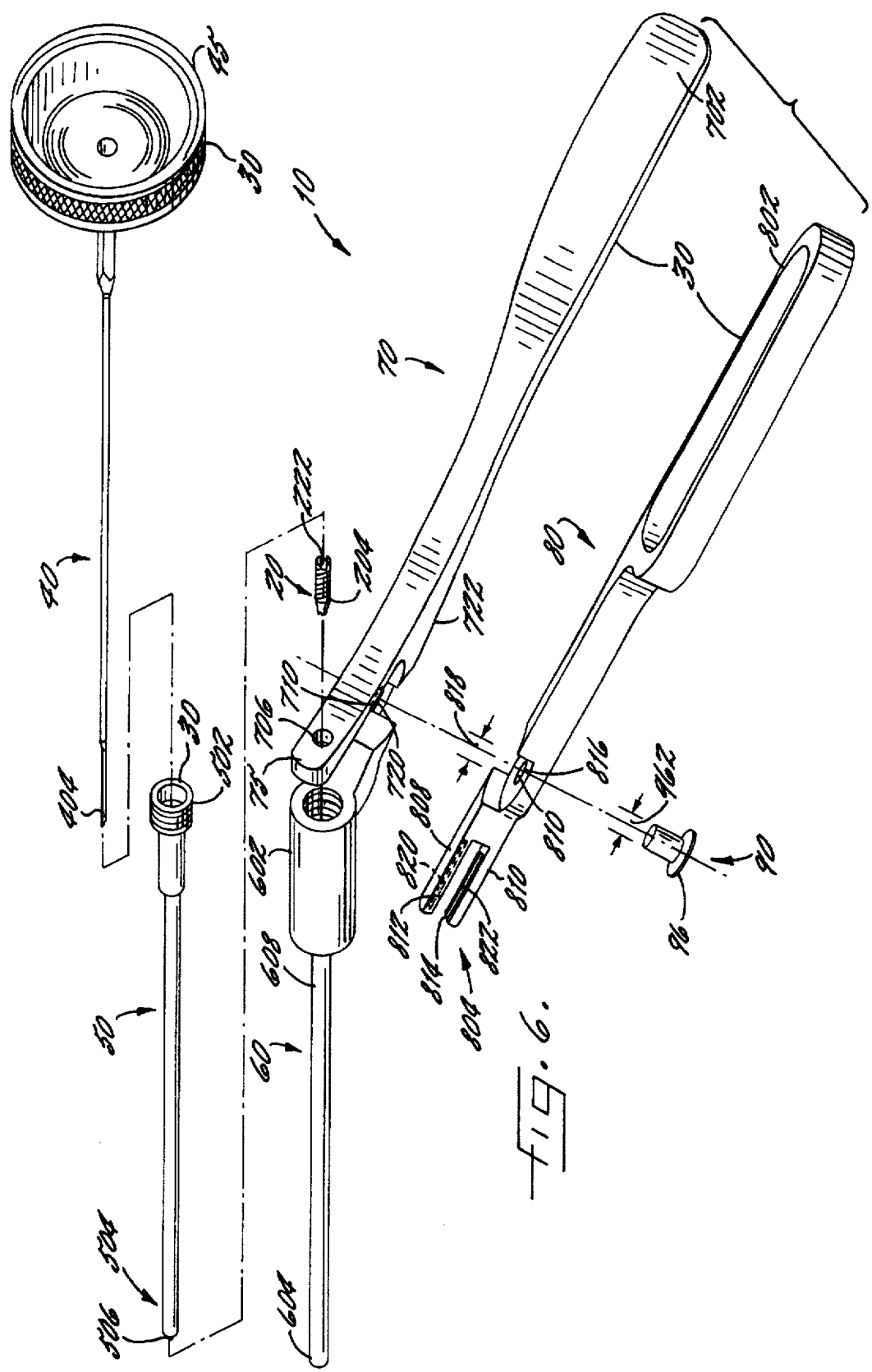

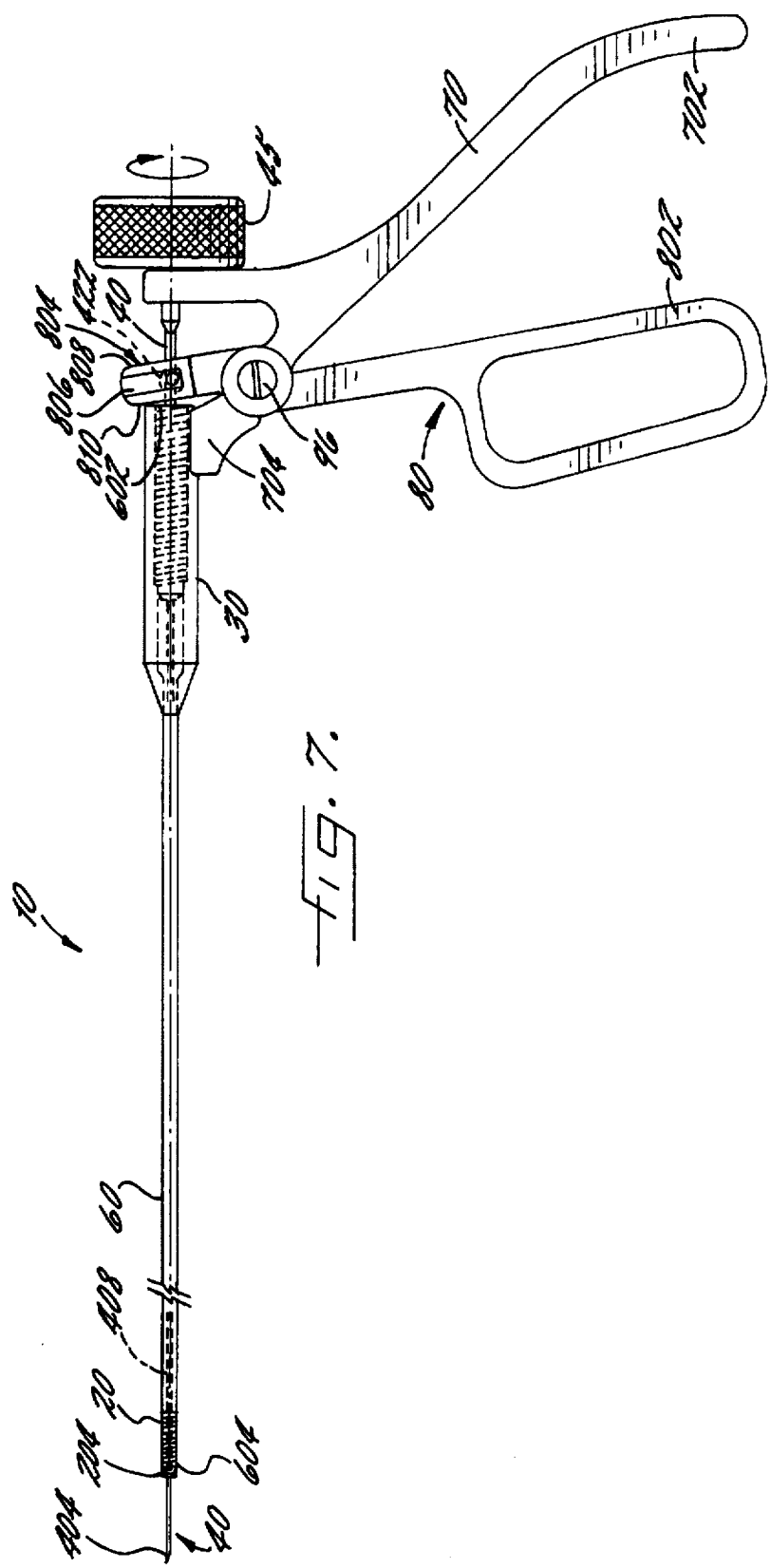

SOFT TISSUE SCREW, DELIVERY DEVICE, AND METHOD

CROSS-REFERENCE TO RELATED APPLICATION

This application is a continuation-in-part of application, "Device for Repairing a Mensical Tear in a Knee and Method," Ser. No. 08/312,999, filed on Sep. 27, 1994, now U.S. Pat. No. 5,569,252, issued on Oct. 29, 1996.

BACKGROUND OF THE INVENTION

1. Field of the Invention

The present invention relates to surgical devices and methods for repairing tissue tears and, more particularly, to a device and method for repairing a meniscal tear in a knee.

2. Description of Related Art

The meniscal of the knee are C-shaped disks of cartilaginous tissue interposed between the condyles of the tibia and the femur. They are actually extensions of the tibia that serve to deepen the articular surfaces of the tibial plateau to accommodate better the condyles of the femur (see FIG. 1). The material of the menisci is collagenous, and the fibers are oriented generally circumferentially.

As the menisci were long considered functionless remains of leg muscle, injury to this tissue had been treated by their total removal, called meniscectomy. A better understanding of these structures, combined with improvements in arthroscopic surgical techniques, has led to the development of meniscal repair techniques.

Posterior peripheral tears of the menisci may be treated by an open technique, wherein sutures are placed along the tear. An arthroscopic technique may also comprise placing sutures along the tear, but in this method through a cannula.

There are a number of fastener-type devices that are known in the art. A surgical fastener is disclosed by Screiber (U.S. Pat. No. 4,873,976) that comprises a shaft having at least one barb for locking the shaft in place when inserted into soft tissue. Also described is an applicator consisting of a cylinder into which the fastener is placed and out of which the fastener is pushed when positioned at the tear site.

Bays et al. (U.S. Pat. Nos. 4,884,572 and 4,895,148) describe a surgical-repair tack and applicator and method of using them. The tack has a barb member and is made of biodegradable material having a degradation time selected to coincide with the healing time of the tissue. In an alternate embodiment, the tack's barb comprises a continuous helical barb.

The method and apparatus for repairing a meniscal tear disclosed by Winters (U.S. Pat. No. 5,059,206) comprises a fastener having protrusions or barbs that is applied to a meniscal tear with a delivery device. The delivery device has a flexible tip that is manipulable through a curved radius to enable the surgeon to insert the device into the central part of the knee and then extend the fastener radially outward into and across a meniscal tear.

SUMMARY OF THE INVENTION

It is an object of the present invention to provide a bioabsorbable fastener, delivery device, and method for repairing a tear in soft tissue.

It is a further object to provide such a fastener that is made from a nontoxic, biocompatible, bioabsorbable plastic specially designed to maintain its structural integrity during the healing of the tear and to prevent tissue abrasion.

It is an additional object to provide such a fastener having a shape designed to compress the tear.

It is another object to provide such a fastener shaped to resist forces tending to pull apart the meniscal tear during healing.

These and other objects are attained with the fastener and delivery device system and method of the present invention.

The fastener of the present invention is designed for repairing a tear in soft tissue of a patient, a particular exemplary embodiment comprising a meniscal tear in a knee. The fastener has a proximal end, a distal end, and a distal portion having a narrowing cross section toward the distal end. In use an insertion of the fastener into soft tissue is facilitated by this narrowed distal end, which takes the form in a preferred embodiment of a conical shaped distal tip.

The fastener further has a variable-pitch helical protrusion along a central portion between the proximal end and the distal end, the helical pitch along the central portion decreasing from the distal end to the proximal end. In use such a decrease in the helical pitch can serve to bring two sides of the tear into apposition as the fastener is advanced across the two sides of the tear in a screwing motion.

In an alternate embodiment of the fastener, the variable-pitch helical protrusion has means for resisting an axial force from pulling the fastener out of the tear and from pulling the two sides of the tear apart. Specifically, the resisting means comprises the helical protrusion having a buttress form.

In a preferred embodiment, the fastener material comprises a biodegradable plastic biocompatible with the soft tissue of the patient. The material is specifically designed to be biodegradable within a first time span greater than or equal to a second time span over which the sides of the tear can knit together. This feature permits the fastener to remain in place for as long as required for the tear to heal, but ultimately to biodegrade and be dissipated harmlessly into the patient's system.

The material is further designed to have elastomeric properties compliant with those of the meniscus in order to confer biofunctionality.

A further feature of the present invention comprises a delivery device for introducing the above-described fastener into the area of the patient's soft tissue to be repaired. A feature of the fastener permitting a mating with a delivery device comprises the fastener's having an axial bore therethrough generally along the helical axis proceeding from the proximal end to the distal end. The bore has a noncircular cross-sectional shape so that an elongated driving device having a noncircular cross-sectional shape can pass into the bore. The fastener can then be advanced into the soft tissue by being rotated by the driving device in a direction having a handedness commensurate with the helically shaped protrusion. Simply put, the fastener appears as a variable-pitch screw that is internally drivable by rotation of an elongated member inserted into its bore.

An additional or alternate feature of the fastener also permitting a mating with a delivery device comprises a notch at the proximal end. The notch enables a mating with a driving device having a protrusion dimensioned to fit within the notch. The fastener is thereby drivable by a rotation of the driving device in a direction having a handedness commensurate with the helically shaped protrusion. Simply put, the fastener in this embodiment is driven in similar fashion to the driving of a screw by a screwdriver. As an alternate embodiment, the delivery device has a notch at its distal end, and the fastener, a protrusion dimensioned to fit within the notch.

The elongated driving device of the present invention for driving the fastener as described above has a distal end, having means for mating with the fastener proximal end, and a proximal end, having means for being rotationally driven. In use the fastener is mated with the driving device distal end, the fastener and distal end of the driving device are positioned adjacent the tear, and the means for being driven is rotated in a direction having a handedness commensurate with the helically shaped protrusion, thereby advancing the fastener across the tear.

In a specific embodiment of the system, the driving device further has a noncircular cross-sectional shape along a distal portion adjacent the distal end. The fastener bore as described above has a noncircular cross-sectional shape dimensioned to permit the distal portion of the driving device to pass into the bore and to permit relative axial sliding and rotational coupling movement therebetween. The axial slidability permits the driving device to be mated by sliding the driving device distal portion into the fastener bore and to be removed once the tear has been breached by sliding the driving device out of the bore.

The method of the present invention is for repairing a tear in soft tissue of a patient. The method comprises the steps of providing a fastener having the features as described above. The fastener is then inserted into an area of soft tissue adjacent the tear. The distal end of the fastener is manipulated to a position generally normal to a long axis of the tear, and the fastener is driven across the tear in a screwing motion. The decrease in the helical pitch serves to bring two sides of the tear into apposition as the fastener is advanced.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 2(b) is a side perspective view of an alternate embodiment of the fastener of the present invention, having a protrusion at the proximal end.

FIG. 3(a) depicts the needle and knob combination.

FIGS. 3(b)–(e) illustrate the cross-sectional shapes of the needle at points A—A, B—B, C—C, and D—D, respectively.

FIG. 4 is a side view of the tubular driver, with the FIG. 4(a) illustrating the cross-sectional shape along the proximal portion adjacent the threaded portion at A—A.

FIG. 6 is an exploded perspective view of the system elements in position to be combined.

FIG. 7 is a side view of the assembled system.

DETAILED DESCRIPTION OF THE PREFERRED EMBODIMENTS

A description of the preferred embodiments of the present invention will now be presented with reference to FIGS. 1–9.

Figure 1:
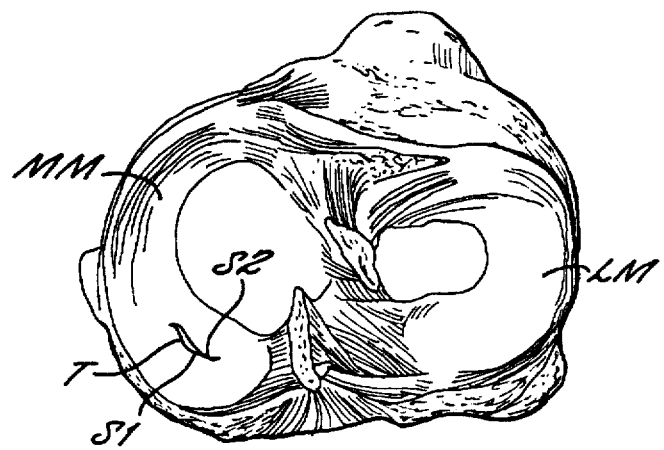
FIG. 1 illustrates the anatomy of a human knee in cross section, showing a tear in the medial meniscus.

The preferred exemplary embodiment of the present invention comprises a fastener, driving device, and method for repairing a knee meniscal tear in a human patient. FIG. 1 illustrates a cross section of a human knee, showing the medial MM and lateral LM menisci and a tear T in the medial meniscus MM, the tear T having two sides S1 and S2.

The system 10 of the present invention comprises a fastener 20 and an elongated driving device 30, shown in exploded and assembled views in FIGS. 6 and 7, respectively.

Figure 2A:
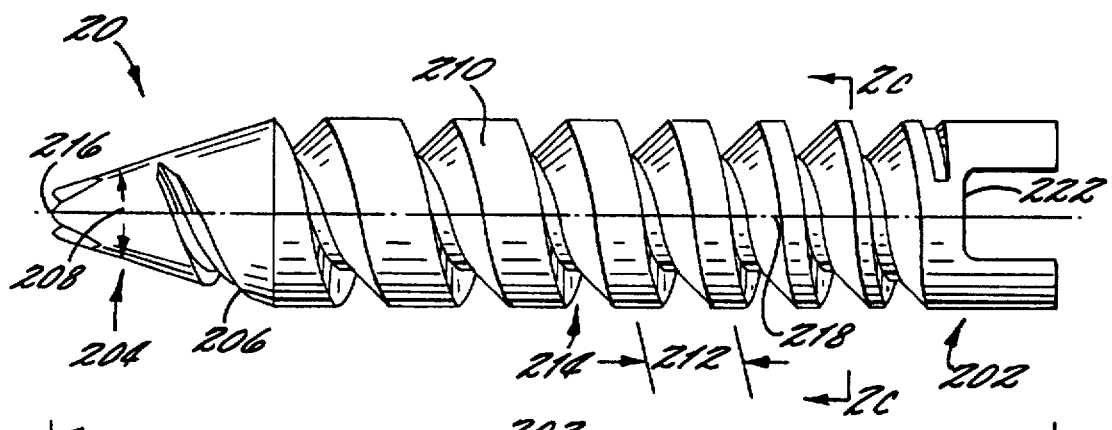
FIG. 2(a) is a side perspective view of the fastener of the present invention.

In a preferred embodiment shown in FIG. 2(a), the fastener 20 has a proximal end 202, a distal end 204, and a length 203. Fastener 20 further has a distal portion 206 having a narrowing cross section 208 toward distal end 204, in this specific embodiment the distal portion 206 forming a cone. Alternatively, a self-tapping distal portion could be implemented. In use an insertion of fastener 20 into soft tissue is facilitated by the conical-shaped distal portion 206.

Along a central portion 214 between proximal end 202 and distal end 204, fastener 20 has a variable-pitch helical protrusion 210. The helical pitch 212 along central portion 214 decreases from distal end 204 to proximal end 202. In use the decrease in helical pitch 212 serves to bring two sides S1, S2 of the tear T into apposition as fastener 20 is advanced across the two sides S1, S2 of the tear T in a screwing motion.

Figure 9A:
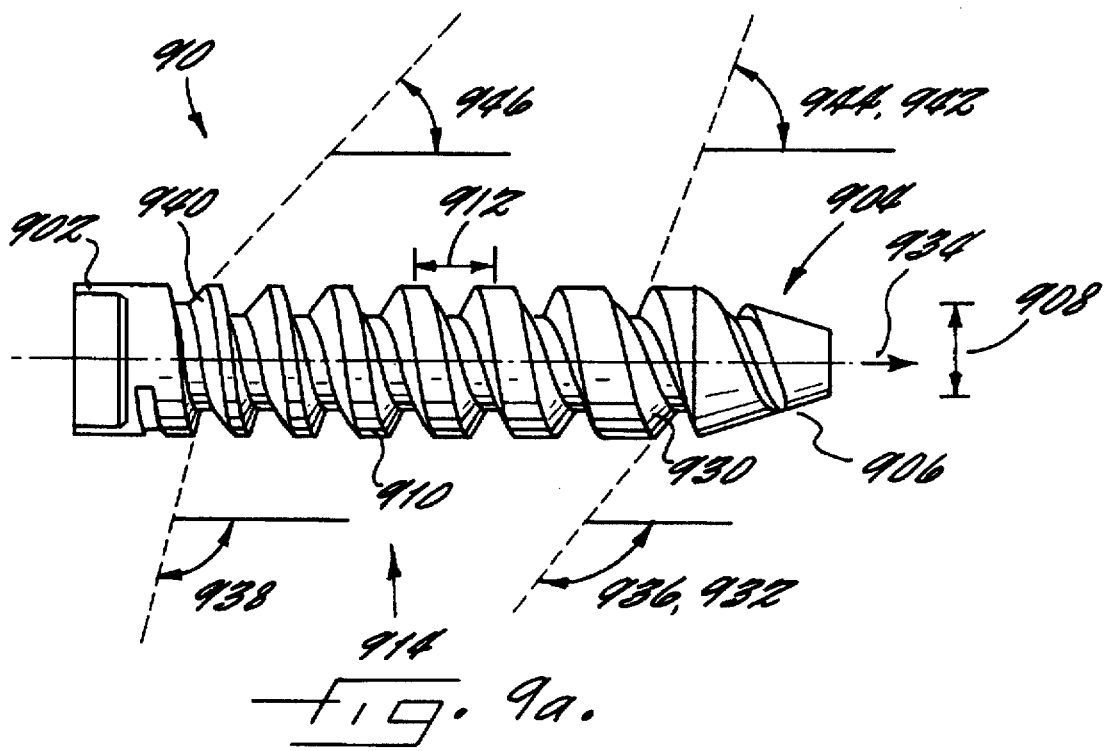
FIG. 9 illustrates an alternate fastener having a buttress form in (a) side perspective view and (b) perspective view from the distal end.
Figure 9B:
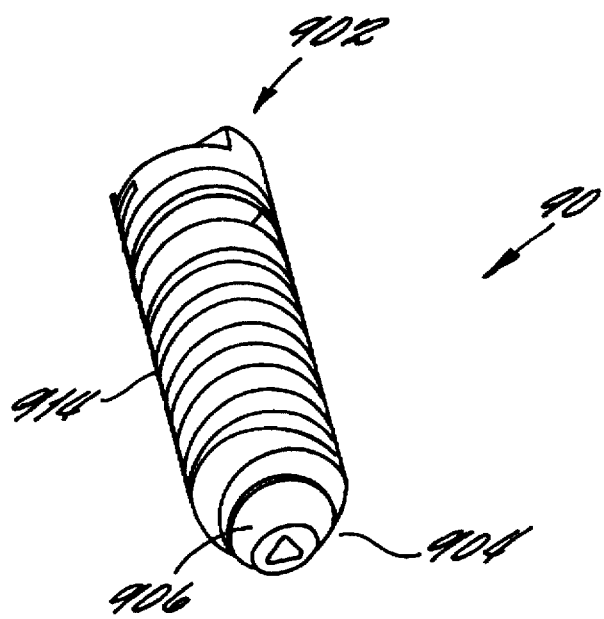

An alternate embodiment of the fastener, shown in FIG. 9(a) and (b), has a buttress form of helical protrusion for resisting an axial force from pulling the fastener out of the tear and from pulling the two sides of the tear apart.

In this embodiment, the fastener 90 has a proximal end 902, a distal end 904, and a length 903. Fastener 90 further has a distal portion 906 having a narrowing cross section 908 toward distal end 904, in this specific embodiment the distal portion 906 forming a cone. Alternatively, a self-tapping distal portion could be implemented. In use an insertion of fastener 90 into soft tissue is facilitated by the conical-shaped distal portion 906.

Along a central portion 914 between proximal end 902 and distal end 904, fastener 90 has a variable-pitch helical protrusion 910. The helical pitch 912 along central portion 914 decreases from distal end 904 to proximal end 902. As with the embodiment shown in FIG. 2, in use the decrease in helical pitch 912 serves to bring two sides S1, S2 of the tear T into apposition as fastener 90 is advanced across the two sides S1, S2 of the tear T in a screwing motion.

As discussed above, this fastener embodiment 90 has means for resisting an axial force wherein the helical protrusion can be described as having a "buttress form," a term known in the art of tool making. The buttress form is known to have advantages in applications involving high stresses along the longitudinal (helical) axis in one direction. The "pressure flank," the face of the protrusion taking the thrust, is generally desired to be nearly perpendicular to the helical axis so that the radial component of the thrust is reduced to a minimum.

In fastener 90 the helical protrusion 910 further has a leading face 930 facing the distal end 904. The leading face 930 makes a first angle 932 with a helical axis vector 934 having a directionality pointing from the proximal 902 to the distal end 904. The first angle 932 decreases from a first oblique angle 936 adjacent the distal end 904 to a second oblique angle 938 adjacent the proximal end 902. The second oblique angle 938, which generally is in the range of 85–90 degrees, is smaller than the first oblique angle 936. The resisting means here then comprises the leading face 930 adjacent the proximal end 902, which serves to resist an axial force in the direction of the helical axis vector 934.

In fastener 90 the helical protrusion 910 further has a trailing face 940 facing the proximal end 902. The trailing face 940 makes a second angle 942 with the helical axis vector 934. The second angle 942 decreases from a first acute angle 944 adjacent the distal end 904 to a second acute angle 946 adjacent the proximal end 902. The second acute angle 946 is smaller than the first acute angle 944. The first acute angle 944 is generally in the range of 85–90 degrees. The resisting means here then further comprises the trailing face 940 adjacent the distal end 904, which serves to resist an axial force in a direction opposite the direction of the helical axis vector 934.

The fastener material in the preferred embodiment comprises a biodegradable plastic biocompatible with the soft tissue of the patient. Exemplary materials include a nontoxic blend of polycaprolactone and polyglycolide, a blend of polylactide and polyglycolide, pure polydioxanone, poly(ethylene oxide):poly(butylene terephthalate), polyorthoester, polyhydroxybutyrate, or cross-linked collagen. The material is designed to be sufficiently flexible and strong to withstand natural knee movement during healing. The material is also designed to be biodegradable within a first time span greater than or equal to a second time span over which the sides S1, S2 of the tear T can knit together. In other words, the material is resorbed over a time span commensurate with the healing process, so that, once the tear T is healed, the fastener 20 can gradually degrade, leaving a healed meniscus with no foreign material embedded therein.

Figure 2C:
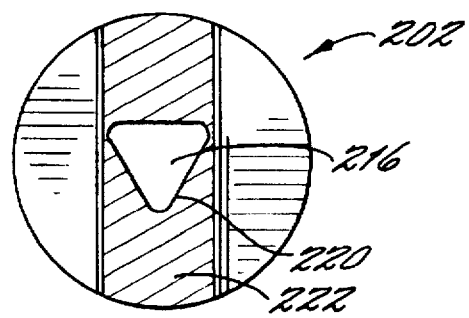
FIG. 2(c) is a cross-sectional view of the fastener of FIG. 2(a) along A—A.

In the preferred embodiment, fasteners 20 (and 90) further have an axial bore 216 (916) therethrough generally along the helical axis 218 (934). (The following discussion will continue only for the fastener embodiment 20, as the remaining elements and features are common to both embodiments 20 and 90, and therefore do not bear repeating.) Bore 216 proceeds from proximal end 202 to distal end 204, and has a noncircular cross-sectional shape to permit an elongated driving device having a noncircular cross-sectional shape to pass into bore 216 and to advance fastener 20 into the meniscus M by being rotated in a direction having a handedness commensurate with the helically shaped protrusion 210 (see FIG. 7). The cross-sectional shape 220 shown in FIG. 2(c) is triangular.

Fastener 20 further has a notch 222 at proximal end 202 for mating with a driving device having a protrusion dimensioned to fit within notch 222. Fastener 20 is thereby drivable by a rotation of the driving device in a direction having a handedness commensurate with the helically shaped protrusion, not unlike the action of a screwdriver on a screw.

As mentioned above, an alternate embodiment, shown in FIG. 2(b) comprises the fastener 20 having a protrusion 225 at the proximal end 202 for mating with a notch in a driving device.

The driving device of the preferred embodiment comprises an elongated driving device 30 comprising a needle 40 inserted through an elongated tubular member 50.

The needle 40 has a length 406, a proximal end 402, and a pointed distal tip 404 (see FIG. 3(a)). Needle 40 further has a cross-sectional triangular shape 408 along a distal portion 410 dimensioned axially to be slidable through the bore 216 of the fastener 20 and rotationally to drive the fastener 20 (A—A, FIG. 3b). Needle 40 has circular cross-sectional shapes 412 and 413 along a central portion 414 (B—B, FIG. 3c) and along a first proximal portion 418 (D—D FIG. 3c) adjacent proximal end 402 and a square cross-sectional shape 416 along a second proximal portion 420 (C—C FIG. 3d) distal of first proximal portion 418. Between first 418 and second 420 proximal portions, needle 40 further comprises a bulge 422 having a larger cross-sectional area than both the first 418 and the second 420 proximal portions, the purpose of which will be described in the following.

In use needle 40 is axially movable distalward to a first position wherein the needle tip 404 protrudes from distal end 204 of fastener 20 (see FIG. 7). In this position, needle tip 404 can pierce the tissue to be repaired, aiding in advancing fastener 20, preparatory to rotating needle 40 and hence fastener 20, which are rotationally coupled.

System 10 further comprises a means for rotationally driving needle 40 connectable to the needle proximal end 402. In the preferred embodiment this rotating means comprises a knob 45 to whose distal side 452 is affixed a cylindrical protrusion 454 having a bore 456 dimensioned to permit first proximal portion 418 of needle 40 to slide therein and be affixed thereinto.

System 10 additionally comprises an elongated tubular member 50 for further rotationally and also for axially driving fastener 20 (see FIG. 4). Tubular member 50 has a distal end 504, matable with the proximal end of fastener 20. Specifically, distal end 504 comprises a raised protrusion 506 dimensioned to fit within the notch 222 of fastener 20 [FIG. 2(a)]. Axial driving is accomplished by pushing tubular member 50 against fastener 20; rotational driving, by turning tubular member 50 in a direction having a handedness commensurate with the helically shaped protrusion, as described above to be not unlike the action of a screwdriver on a screw.

Tubular member 50 further has a proximal end 502 and a threaded proximal portion 508 adjacent proximal end 502, threaded portion 508 having a length 510. Additionally, tubular member 50 has an axial bore 512 therethrough from distal end 504 to proximal end 502, at least a portion 516 of which adjacent threaded proximal portion 508 is noncircular. The bore 512 is dimensioned to permit needle 40 to pass therethrough and to be relatively slidable axially, and the noncircular portion 516, which in this embodiment is square (inset A—A, FIG. 4a), is dimensioned to be rotatably drivable by needle 40 via square cross section 416.

Tubular member 50 has a length 518 shorter than needle length 406, permitting distal end 404 and proximal end 402 of needle 40 to protrude from distal end 504 and proximal end 502, respectively, of tubular member 50 (see FIG. 7).

Figure 5:
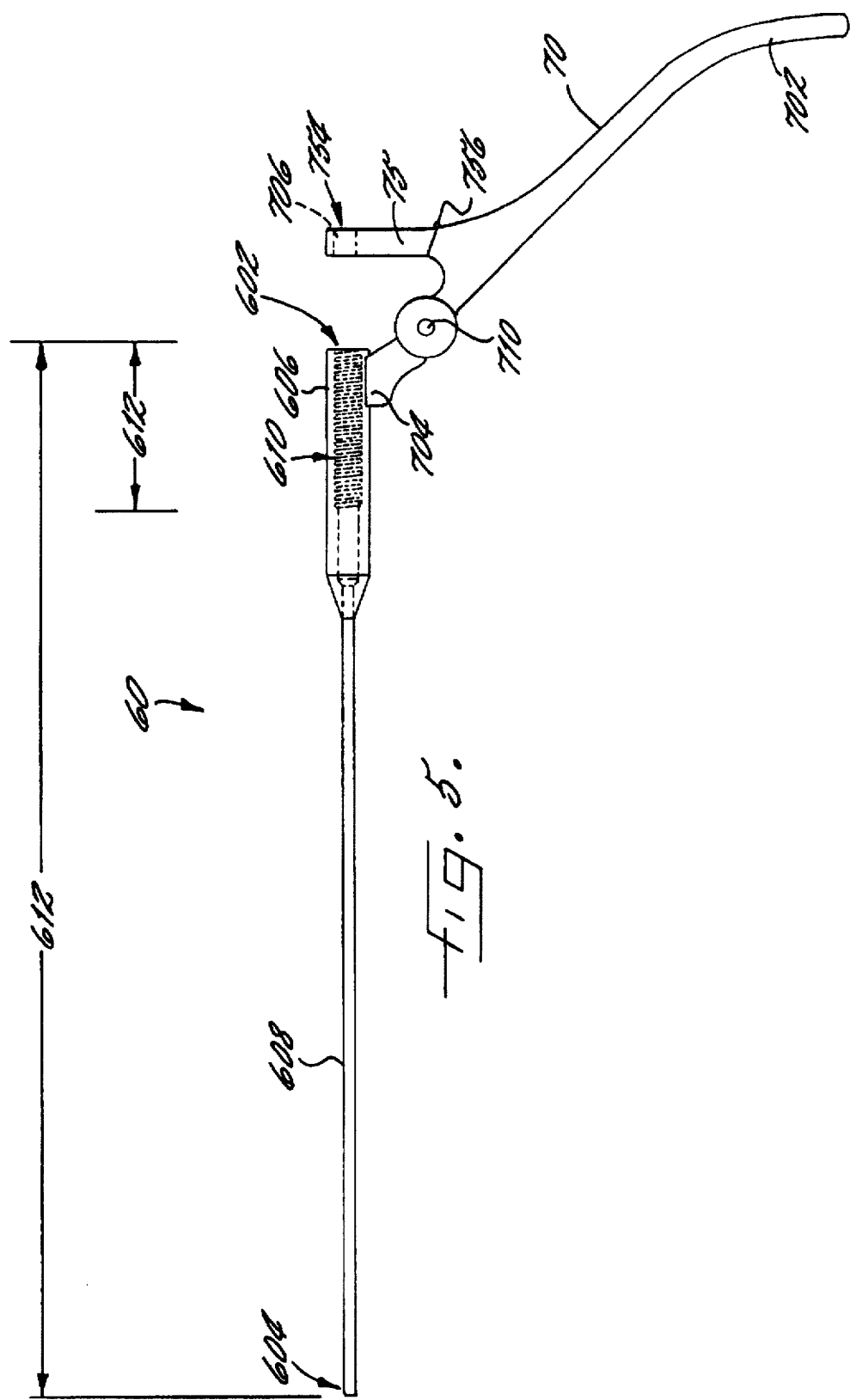
FIG. 5 is a side view of the cannula and first gripping member combination.

A further component of system 10 and driving device 30 comprises a cannula member 60 for protecting fastener 20 during insertion into the soft tissue area adjacent the tear T (see FIG. 5). Cannula a member 60 has a proximal end 602 and a distal end 604.

In addition, cannula member 60 has an axial bore 608 therethrough from distal end 604 to proximal end 602. Bore 608 is dimensioned to permit tubular member 50 and fastener 20 to fit therein and to permit sliding and rotational movement therebetween.

Cannula member 60 further has a proximal portion 606 movingly affixable to proximal end 502 of tubular member 50. In particular, bore 608 of cannula member 60 has a threaded proximal portion 610 dimensioned to permit the threaded proximal portion 508 of tubular member 50 to travel therealong. Threaded proximal portion 610 has a length 612 greater than the length 510 of the tubular member threaded proximal portion 508. When tubular member threaded portion 508 is threaded into cannula member threaded portion 610, and needle 40 is inserted into tubular member 50 so that the square cross-sectional area 416 and square bore portion 516, respectively, coincide, there is provided a means for transducing a rotational movement of needle 40 into an axial movement of tubular member 50. Via these means, such a rotational movement drives an axial movement of fastener 20 and further drives a rotational movement of fastener 20 via needle 40.

Specifically, the means for transducing comprises a rotation of needle 40, the square cross-sectional portion 416 rotationally driving the square cross-sectional bore portion 516. This then causes a relative axial movement between tubular member 50 and cannula member 60 via the mated threaded proximal portion 508 and bore 610, respectively, which causes a pushing of fastener 20 by tubular member 50 and thereby a consequent relative axial movement between fastener 20 and cannula member 60.

Cannula member 60 has a length 612 shorter than needle length 406, permitting distal tip 404 and proximal end 402 of needle 40 to protrude from distal end 604 and proximal end 602, respectively, of cannula member 60. Cannula member length 612 is further longer than the tubular member length 518 by at least the length 203 of fastener 20, permitting the mated fastener 20 and tubular member 50 both to reside within the cannula bore 608 (see FIG. 7).

The difference in the lengths of the tubular member threaded proximal portion 508 and cannula member bore threaded proximal portion 610 is greater than or equal to the length of fastener 20. This difference permits fastener 20 to be driven axially from a first position wherein distal end 204 of fastener 20 is adjacent distal end 604 of cannula a member 60 to a second position wherein proximal end 202 of fastener 20 is distal of distal end 604 of cannula member 60 (see FIG. 8).

A further component of system 10 comprises gripping means affixed to proximal end 602 of cannula a member 60 for facilitating an operator's use of the system. In the preferred embodiment the gripping means comprises a first 70 and a second 80 gripping member and hinge means 90 for connecting first 70 and second 80 gripping members at respective hinge points 710 and 810.

First gripping member 70 has a lower end 702 for gripping and an upper end 704 affixed adjacent proximal end 602 of cannula member 60. First gripping member 70 further has attached to it an arm 75 extending upward from a point below hinge point 710 to a top end 754 at a point proximal of upper end 704, thereby forming a "Y"-shaped member. Arm top end 754 has means for supporting first proximal portion 418 of needle 40, specifically, for supporting cylindrical protrusion 454 of knob 45, within whose bore 456 first proximal portion 418 of needle 40 is affixed. This support means comprises a bore 706 coaxial with cannula bore 608, bore 706 dimensioned to permit protrusion 454 to fit therethrough and be rotatable therein. In this embodiment, arm 75 is hingedly affixed to member 70 via hinge 756, positioned to permit a proximal movement of arm 75 during assembly of system 10 (see below).

Second gripping member 80 has a lower end 802 for gripping and an upper end 804 for supporting and axially restraining needle 40 between first 418 and second 420 proximal portions (see FIGS. 6 and 7). The needle support comprises a notch 806 through upper end 804 from the proximal side 808 to the distal side 810 by which needle 40 may be supported. A pair of grooves 820 and 822 in the opposed faces 812 and 814 of notch 806 are dimensioned to permit bulge 422 to be slidable in an upward and downward direction but restrained in an axial direction. Therefore, an axial movement of second gripping member 80 will cause an axial movement of needle 40.

Hinge means 90 comprises screw 96 connecting first 70 and second 80 gripping members. Second gripping member 80 has a bore 816 therethrough from a first 808 to a second 810 side at hinge point 810. Bore 816 has a circular cross section having a diameter 818 greater than the diameter 962 of screw 96. First gripping member 70 has a threaded bore 720 proceeding from the second side 722 dimensioned to permit screw 96 to be threaded thereinto. Thus, the hinge points 710 and 810 being situated between the upper 704, 804 and the lower ends 702,802, respectively, permits movement therebetween in a scissorslike fashion. Gripping members 70 and 80 are thereby movable relatively from a first position wherein upper end 804 of second gripping member 80 is disposed in spaced relation from upper end 704 of first gripping member 70. The needle 40 is thereby in a most proximal position. Gripping members 70 and 80 are then movable relatively to a second position wherein upper end 804 of second gripping member 80 is disposed adjacent upper end 704 of first gripping member 70. The needle 40 in this second position is then in a most distal position, as shown in FIG. 7.

The assembly of system 10 is shown in FIG. 6 and the fully assembled system 10 in FIG. 7. Fastener 20 is affixed to tubular member distal end 504 by inserting protrusion 506 into notch 222. The combined fastener 20 and tubular member 50 are inserted, fastener 20 first, into cannula 60, with arm 75 moved so as not to impede this insertion. These elements are dimensioned relatively so that, when thus inserted, fastener distal end 204 and cannula distal end 604 generally coincide. Arm 75 is then moved upward so that bore 706 is coaxial with cannula bore 608. Needle 40 is inserted, distal tip 404 first, through arm bore 706 and into the proximal end 502 of tubular member 50 until knob 45 is positioned adjacent arm 75. Second gripping member 80 is then affixed to first gripping member 70 with screw 96, with upper end 804 positioned so that bulge 422 is restrained within grooves 820 and 822.

Referring to FIG. 7, it can be seen that the dynamics of the assembled system operate as follows: Needle 40 is advanced distalward by moving the upper end 804 of second gripping member 80 from the first position to the second position, i.e., distalward, which, being coupled to bulge 422, forces distal tip 404 beyond the distal end 604 of cannula 60.

Next, turning knob 45, and thus needle 40, drives three movements, two rotational and one axial:
1. Needle triangular cross section 408 rotates fastener via the rotational coupling with fastener bore 216;
2. Needle square cross section 416 rotates tubular member 50 via square bore portion 516 and thus fastener 20 via mated notch 222 and protrusion 506;

3. Rotation of tubular member 50 causes relative axial movement against cannula 60 via mated threaded portions 508 and 610, which then causes an axial movement of fastener 20 versus cannula a 60; when the rotation has a handedness commensurate with the handedness of the threaded portions 508 and 610, this causes an extrusion of the fastener 20 out of cannula bore 608.

In the embodiment contemplated for repairing a knee meniscus, the needle, the tubular member, and the cannula a member all similarly have a curve therein for enabling an operator to manipulate the system into a position to approach a soft tissue tear around a curved radius, as will be shown in the discussion and in FIG. 8 on the method of the present invention. In the preferred embodiment, this curve comprises a 10–30 degree generally upward bend.

Figure 8A:
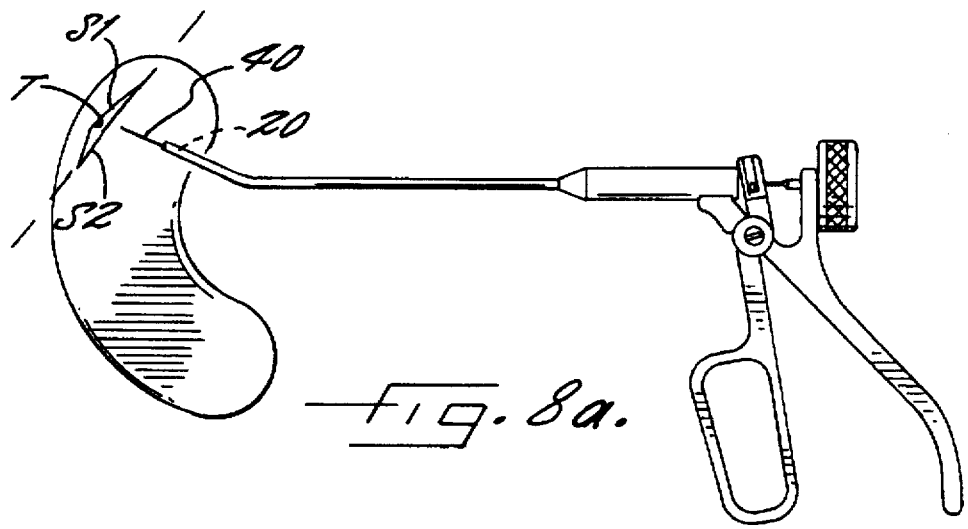
FIG. 8 illustrates the method for repairing a knee meniscal tear (a) The needle, moved out of the fastener bore, approaching the tear; (b) the needle piercing the tissue to be repaired; (c) the fastener driven across the tear; (d) the two sides of the tear brought into apposition as the fastener is advanced.

The method of the present invention for repairing a tear T in soft tissue of a patient, shown in FIG. 8 for repairing a meniscal tear, comprises the steps of providing a fastener 20 and a needle 40 as described above and shown in FIGS. 2 and 4, here shown in the bent embodiment [FIG. 8(a)]. The needle 40 is then moved axially through the bore 216 of the fastener 20, the distal tip 404 of the needle 40 emerging from the distal end 204 of the fastener 20.

The fastener 20 is inserted into the knee in an area of soft tissue adjacent the tear T. The operator then manipulates the distal end 204 of the fastener 20 to a position generally normal to the long axis A of the tear T.

Figure 8B:
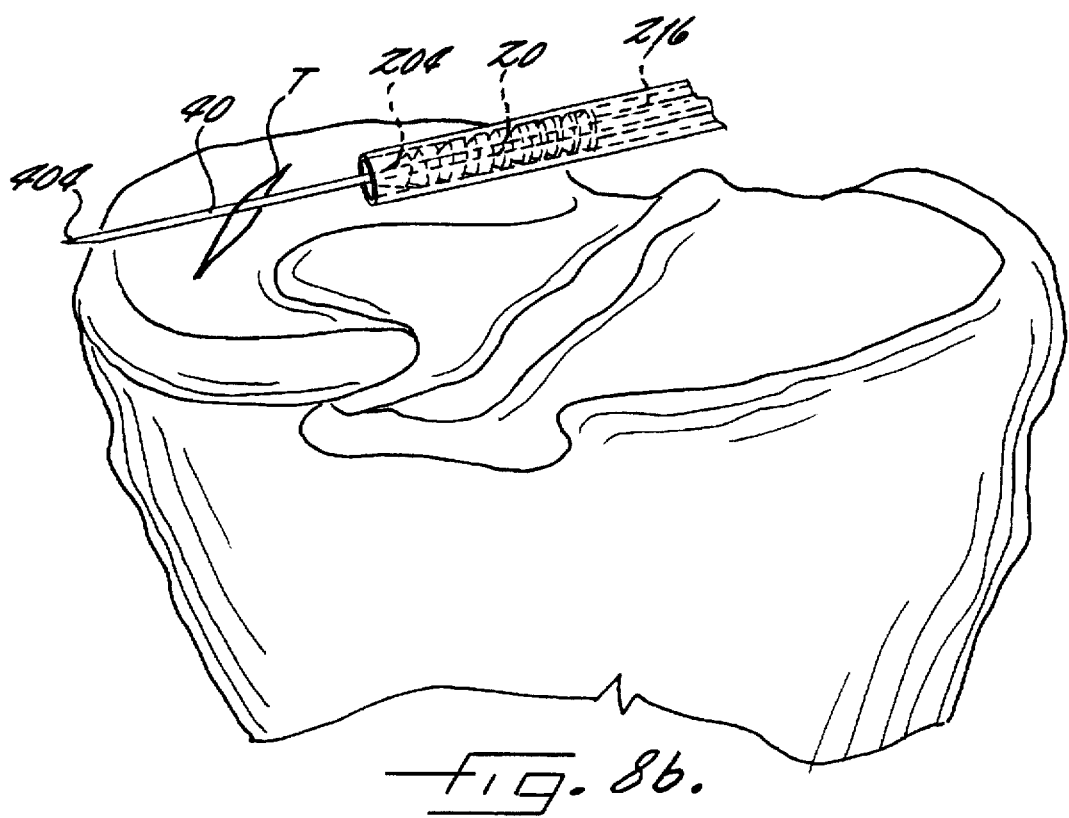
Figure 8C:
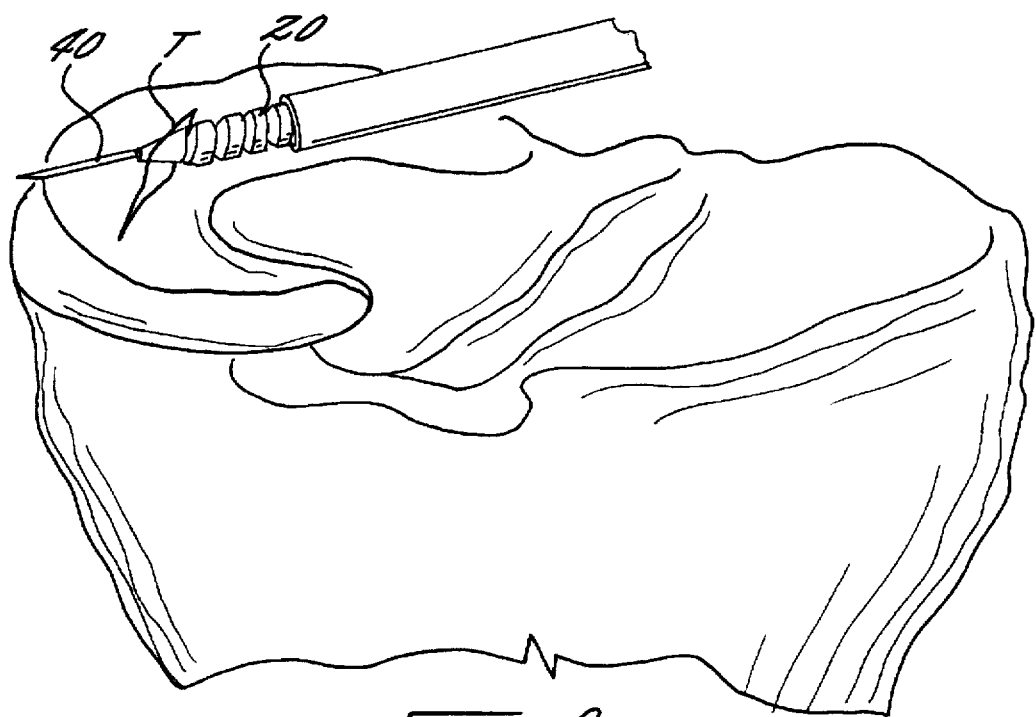
Figure 8D:
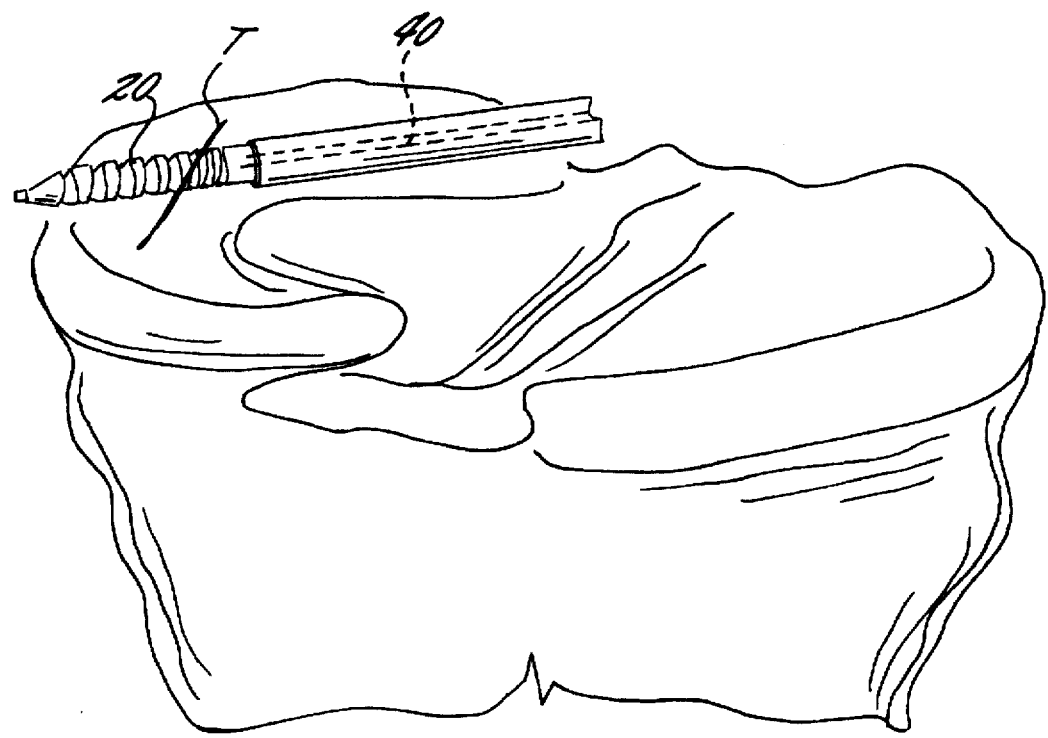

The next steps comprise piercing the tissue to be repaired with the needle distal tip 404 [FIG. 8(b)] and driving the fastener 20 across the tear T in a screwing motion [FIG. 8(c)], the decrease in the helical pitch 212 serving to bring two sides of the tear S1,S2 into apposition as the fastener 20 is advanced [FIG. 8(d)]. Given the rotationally coupled needle 40 and fastener 20, the driving step comprises rotating the needle 40 and hence the fastener 20. Since the needle 40 and fastener 20 are axially slidable relative to each other, the needle 40 can then be removed from the fastener 20 and all instruments removed from the surgical site once the sides of the tear have been drawn together.

It may be appreciated by one skilled in the art that additional embodiments may be contemplated, including fasteners, systems, and methods for repairing other soft tissue tears, such as in the shoulder.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and method illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A fastener for repairing a tear in soft tissue of a patient, the fastener having:
    a proximal end;
    a distal end;
    a distal portion having a narrowing cross section toward the distal end, wherein in use an insertion of the fastener into soft tissue is facilitated by the narrowed distal end;
    a variable-pitch helical protrusion along a central portion between the proximal end and the distal end, the helical protrusion having:
        a helical pitch along the central portion, the helical pitch decreasing from the distal end to the proximal end, wherein in use the decrease in the helical pitch tends to bring two sides of the tear into apposition as the fastener is advanced across the two sides of the tear in a screwing motion;
    means for resisting an axial force from pulling the fastener out of the tear and from pulling the two sides of the tear apart; and
    a leading face facing the distal end, the leading face making a first angle with the helical axis vector having a directionality pointing from the proximal end to the distal end, the first angle decreasing from a first oblique angle adjacent the distal end to a second oblique angle adjacent the proximal end, the second oblique angle smaller than the first oblique angle, the resisting means comprising the leading face adjacent the proximal end for resisting an axial force in the direction of the helical axis vector; and
    an axial bore therethrough generally along a helical axis vector proceeding from the proximal end to the distal end, the bore having a noncircular cross-sectional shape for permitting an elongated driving device having a noncircular cross-sectional shape to pass substantially completely through the bore and to advance the fastener into the soft tissue by being rotated in a direction having a handedness commensurate with the helically shaped protrusion.

2. The fastener recited in claim 1, wherein the helical protrusion further has a trailing face facing the proximal end, the trailing face making a second angle with the helical axis vector, the second angle decreasing from a first acute angle adjacent the distal end to a second acute angle adjacent the proximal end, the second acute angle smaller than the first acute angle, the resisting means further comprising the trailing face adjacent the distal end for resisting an axial force in a direction opposite the direction of the helical axis vector.

3. The fastener recited in claim 2, wherein the fastener material comprises a biodegradable plastic biocompatible with the soft tissue of the patient and further biodegradable within a first time span greater than or equal to a second time span over which the sides of the tear can knit together.

4. The fastener recited in claim 1, wherein the cross-sectional shape of the axial bore is triangular.

5. The fastener recited in claim 1, wherein the fastener further has a notch at the proximal end for mating with a driving device having a protrusion dimensioned to fit within the notch, the fastener thereby being drivable by a rotation of the driving device in a direction having a handedness commensurate with the helically shaped protrusion.

6. A system for repairing a tear in soft tissue of a patient, the system comprising:
    a fastener having:
        a proximal end;
        a distal end;
        a distal portion having a narrowing cross section toward the distal end, wherein in use an insertion of the fastener into soft tissue is facilitated by the narrowed distal end;
        a variable-pitch helical protrusion along a central portion between the proximal end and the distal end, the helical protrusion having:
            a helical pitch along the central portion, the helical pitch decreasing from the distal end to the proximal end, wherein in use the decrease in the helical pitch tends to bring two sides of the tear into apposition as the fastener is advanced across the two sides of the tear in a screwing motion; and means for resisting an axial force from pulling the fastener out of the tear and from pulling the two sides of the tear apart; an elongated driving device comprising:

a needle having:
  a length;
  a proximal end;
  a pointed distal tip; and
  a cross-sectional shape along a distal portion dimensioned axially to pass through the bore of the fastener and rotationally to drive the fastener;
  wherein in use the needle is axially movable distalward to a first position wherein the needle tip protrudes from the distal end of the fastener, the needle tip piercing the tissue to be repaired preparatory to rotating the needle and hence the fastener;

an elongated tubular member for rotationally and axially driving the fastener, the tubular member having:
  a distal end, matable with the proximal end of the fastener;
  a proximal end;
  an noncircular axial bore therethrough from the distal end to the proximal end, at least a portion of which is noncircular, the bore dimensioned to permit the needle to pass therethrough and to be relatively slidable axially, the noncircular portion of the bore dimensioned to be rotatably drivable by the needle; and
  a length shorter than the needle length, permitting the distal end and the proximal end of the needle to protrude from the distal end and the proximal end, respectively, of the tubular member;

means for transducing a rotational movement of the needle into an axial movement of the tubular member; and means for rotating the needle connectable to the needle proximal end, such a rotation thereby driving an axial movement of the fastener via the transducing means and further driving a rotational movement of the fastener via the needle.

7. The system recited in claim 6, further comprising a cannula member for protecting the fastener, the cannula member having:
  a proximal end;
  a proximal portion movingly affixed to the proximal end of the tubular member;
  a distal end;
  an axial bore therethrough from the distal end to the proximal end, the bore dimensioned to permit the tubular member and the fastener to fit therein and to permit sliding and rotational movement therebetween;
  a length shorter than the needle length, permitting the distal end and the proximal end of the needle to protrude from the distal end and the proximal end, respectively, of the cannula member, the length longer than the tubular member length, permitting the mated fastener and tubular member to reside within the bore.

8. The system recited in claim 7, further comprising gripping means affixed to the proximal end of the cannula member for facilitating an operator's use of the system.

9. The system recited in claim 8, wherein the needle has a first proximal portion adjacent the proximal end and a second proximal portion distal of the first proximal portion, and wherein the gripping means comprises:
  a first gripping member having a lower end for gripping and an upper end affixed adjacent the proximal end of the cannula member;
  a second gripping member having a lower end for gripping and an upper end having means for supporting and axially restraining the needle between the first and the second proximal portions; and
  hinge means for connecting the first and the second gripping members at a hinge point between the upper and the lower ends in a scissorslike fashion, the gripping members movable relatively from a first position wherein the upper end of the second gripping member is disposed in spaced relation from the upper end of the first gripping member, the needle thereby in a most proximal position, to a second position wherein the upper end of the second gripping member is disposed adjacent the upper end of the first gripping member, the needle thereby in a most distal position.

10. The system recited in claim 9, wherein the first gripping member further has an arm extending upward from a point below the hinge point to a point proximal of the upper end, thereby forming a "Y"-shaped member, the arm having a top end having means for supporting the first proximal portion of the needle, and wherein the rotating means comprises a knob.

11. The system recited in claim 10, wherein:
  the tubular member has a threaded proximal portion adjacent the proximal end, the threaded portion having a length;
  the bore of the cannula member has a threaded proximal portion dimensioned to permit the threaded proximal portion of the tubular member to travel therealong, the bore threaded proximal portion having a length greater than the length of the tubular member threaded proximal portion;
  the means for transducing comprises a rotation of the needle driving a rotation of the tubular member, thereby causing a relative axial movement between the tubular member and the cannula member and a consequent relative axial movement between the fastener and the cannula member; and
  the difference in the lengths of the tubular member threaded proximal portion and the cannula member bore threaded proximal portion is greater than or equal to the length of the fastener, thereby permitting the fastener to be driven axially from a first position wherein the distal end of the fastener is adjacent the distal end of the cannula member to a second position wherein the proximal end of the fastener is distal of the distal end of the cannula member.

12. The system recited in claim 7, wherein the needle, the tubular member, and the cannula member all similarly have a curve therein for enabling an operator to approach a soft tissue tear around a curved radius.

13. A method for repairing a tear in soft tissue of a patient, the method comprising the steps of:
  providing a fastener having:
    a proximal end;
    a distal end;
    a distal portion having a narrowing cross section toward the distal end, wherein in use an insertion of the fastener into soft tissue is facilitated by the narrowed distal end; and
    a variable-pitch helical protrusion along a central portion between the proximal end and the distal end, the helical protrusion having:

a helical pitch along the central portion, the helical pitch decreasing from the distal end to the proximal end, wherein in use the decrease in the helical pitch tends to bring two sides of the tear into apposition as the fastener is advanced across the two sides of the tear in a screwing motion;

an axial bore therethrough generally along the helical axis proceeding from the proximal end to the distal end, the bore having a noncircular cross-sectional shape and means for resisting an axial force from pulling the fastener out of the tear and from pulling the two sides of the tear apart;

providing an elongated needle having:
a length;
a proximal end;
a pointed distal tip; and
a cross-sectional shape along a distal portion dimensioned axially to pass through the bore of the fastener and rotationally to drive the fastener;

moving the needle axially through the bore of the fastener, the distal tip of the needle emerging from the distal end of the fastener;

inserting the fastener into an area of soft tissue adjacent the tear;

manipulating the distal end of the fastener to a position generally normal to a long axis of the tear;

piercing the tissue to be repaired with the needle tip;

driving the fastener across the tear in a screwing motion by rotating the needle and hence the fastener, the decrease in the helical pitch serving to bring two sides of the tear into apposition as the fastener is advanced.

* * * * *